United States Patent [19]

Gibbons

[11] Patent Number: 4,820,647

[45] Date of Patent: Apr. 11, 1989

[54] METHOD FOR DETECTING A METAL ION IN AN AQUEOUS ENVIRONMENT

[75] Inventor: Ian Gibbons, Menlo Park, Calif.

[73] Assignee: Biotrack, Inc., Mountain View, Calif.

[21] Appl. No.: 937,307

[22] Filed: Dec. 3, 1986

[51] Int. Cl.[4] .................... G01N 21/78; G01N 33/20; G01N 33/50

[52] U.S. Cl. ...................... 436/79; 436/73; 436/74; 436/164

[58] Field of Search .................. 436/73, 74, 79, 164

[56] References Cited

U.S. PATENT DOCUMENTS

| | | | |
|---|---|---|---|
| 3,754,864 | 8/1973 | Gindler | 436/74 |
| 4,367,072 | 1/1983 | Voegtle et al. | 436/805 X |
| 4,382,122 | 5/1983 | Mezei et al. | 436/74 |
| 4,407,962 | 10/1983 | Tobacco et al. | 436/74 |
| 4,436,923 | 3/1984 | Pacey et al. | 436/74 X |
| 4,448,889 | 5/1984 | Neri et al. | 436/74 |
| 4,540,520 | 9/1985 | Charlton et al. | 260/396 N |
| 4,639,424 | 1/1987 | Wong | 436/74 |
| 4,645,744 | 2/1987 | Charlton et al. | 436/74 |
| 4,649,123 | 3/1987 | Charlton et al. | 436/74 X |
| 4,659,815 | 4/1987 | Pacey et al. | 436/74 X |
| 4,703,015 | 10/1987 | Tobacco et al. | 436/74 |
| 4,711,853 | 12/1987 | Pacey et al. | 436/74 |
| 4,734,375 | 3/1988 | Charlton | 436/74 |
| 4,734,376 | 3/1988 | Pacey et al. | 436/74 X |
| 4,742,010 | 5/1988 | Lin et al. | 436/74 |
| 4,762,799 | 8/1988 | Seitz et al. | 436/74 X |

FOREIGN PATENT DOCUMENTS 0153641  9/1985  European Pat. Off. .

OTHER PUBLICATIONS

Wong et al., Clin. Chem., vol. 31, No. 9, pp. 1464–1467, 9/85.
Sumiyoshi et al., Talanta, vol. 24, pp. 763–765, 1977.
Zheng et al., Chemical Abstracts, vol. 104, Abstract No. 104:56803x, 2/24/86.
Zhang et al., Chemical Abstracts, vol. 104, Abstract No. 104:42286u, 2/10/86.
Pilipenko et al., Chemical Abstracts, vol. 96, Abstract No. 96:132551x, 4/82.
Charlton et al., Clin. Chem., vol. 28, No. 9, pp. 1857–1861, 1982.
Hofman, The Function of Bile Salts in Fat Absorption, (1963), Biochem. J., 89: 57–68.
Pacey et al., A New Chrom. Crown Ether 4"-Cyano-2", 6" Dinitro-4'Aminobenzo 15-Crown-5 as an Alkali Metal Extraction Reagent, (1980), Analytical Letters, 13:1085–1091.
Sokolova et al., Phase Sep. in Dip. Phos. Choline in the Presence of Ion and Binary Electrolytes, (1982), Biophysics 27:834–839.

Primary Examiner—Robert J. Hill, Jr.
Attorney, Agent, or Firm—Richard L. Neeley

[57] ABSTRACT

A method for detecting the presence of a metal ion in an aqueous environment, which comprises contacting a micelle-forming material, a hydrophobic or amphiphilic dye, and a hydrophobic ionophore capable of selectively binding the ion with a sample of the aqueous environment to form a mixture and measuring a change in absorbance of light by the dye. Compositions method are also disclosed.

9 Claims, No Drawings

METHOD FOR DETECTING A METAL ION IN AN AQUEOUS ENVIRONMENT

BACKGROUND OF THE INVENTION

1. Field of the Invention

This invention relates to compositions and techniques useful in the measurement of ion concentrations in solution.

2. Description of the Background

Prior to the present invention, numerous methods for determining the concentration of metal ions in solution existed. These included atomic absorbtion photometry, ion-specific electrodes, flame photometry, and classical precipitation techniques.

Among the more recent techniques developed is a solid-phase colorimetric determination of potassium, which involves a nonpolar organic film, typically plasticized polyvinyl chloride, containing the ionophore valinomycin. The film is incubated with an aqueous solution containing potassium ions and a detectable anion, typically erythrosin B. The amount of erythrosin B retained by the film after washing can be measured by absorbance or reflectance and is directly related to the potassium concentration.

A second recently developed technique relies on the extraction of an ion pair into an organic solvent. This spectrophotometric method relies on the selective complexing of potassium by a specific macrocyclic polyether (crown ether), with the subsequent formation of an ion pair with a colored anion. The colored anion is extracted into an organic solvent, and the absorbance is measured to determine the amount of potassium ion present in the original solution.

A number of specific dye-coupled ionophores or dye-ionophore pairs have been prepared or described for use in such systems.

Although both of these new techniques eliminate a number of the disadvantages of prior techniques, such as requirements for a significant amount of wet chemistry or expensive equipment, they nonetheless suffer from several disadvantages. The solvent-extraction method requires the use of an immiscible liquid phase and a corresponding number of separation and clarification steps. The solid-phase method requires the existence of a photometer the reads either reflectance or absorbance in the solid-phase, such instruments being relatively rare in clinical laboratories.

Accordingly, there remains a need for a homogeneous assay capable of detecting the presence of metal ions in aqueous solutions that utilizes standard spectrophotometric equipment.

DESCRIPTION OF RELEVANT LITERATURE

Charlton, *Clin. Chem.*, (1982) 28: 1857–1861 describes a solid-phase colorimetric determination of potassium utilizing a nonpolar organic film containing the ionophore valinomycin utilized in combination with a dye that is retained in the film. Charlton et al. U.S. Pat. No. 4,540,520, describes a number of ionophores useful in this method. Wong et al. *Clin. Chem.* (1985) 31: 1464–1465 and Sumiyoshi, *Talanta* (1977) 24: 763–765, describe colorimetric determinations of potassium in blood serum or whole blood utilizing a solvent-extraction process in which an ion-pair of a complex of a crown ether with potassium and bromocresol green is extracted into an organic solvent. A number of ionophores useful in solvent extraction methods are described in Pacey et al., *Anal. Lett.* (1980) 13: 1085–1091, Pacey et al., U.S. Pat. No. 4,436,923, and Voegtle et al., U.S. Pat. No. 4,367,072. Studies involving lipid layer structure in the presence of ionophores and various salts are repoted in Sokolova et al., *Citologi (Cytology, U.S.S.R.)* (1976) 18: 744–746 and Gracheva et al., *Biophysics* (1982) 27: 834–839. The use of bile salts to increase the solubility of hydrophobic dyes in water is described in Hoffmann, *Biochem. J.* (1963) 89: 57–68.

SUMMARY OF THE INVENTION

The present invention provides a method for detecting the presence of a metal ion in an aqueous environment by contacting a micelle-forming material, a hydrophobic or amphiphilic dye, and a hydrophobic ionophore capable of selectively binding the ion with a sample from the aqueous environment. Two or more of the three components can be part of the same molecule; e.g., an amphiphilic dye can act both as a dye and as a micelle-forming material. Changes in absorbance of light resulting from interactions between the dye and the complex formed between the hydrophobic ionophore and the metal ion are measured to determine the amount of metal ion present in the original aqueous environment.

DESCRIPTION OF PREFERRED EMBODIMENTS

The present invention provides an essentially homogeneous technique for colorimetrically determining the presence of metal ions in aqueous solutions that avoids the necessity of extraction steps as described in the prior art. The method comprises contacting a micelle-forming material, a hydrophobic or amphiphilic dye, and a hydrophobic ionophore capable of selectively binding the target ion with a sample of the aqueous environment to form a mixture and then measuring the change in absorbance of light by the dye. The measurement is made on the essentially homogeneous mixture containing the micelles, which are colloidal in size. The method is quite general, being applicable to any metal ion which can be selectively bound by a hydrophobic ionophore. Furthermore, only the hydrophobicity and ion-binding specificity of the ionophore are important, not its detailed structure, so that the method is not dependent on the specific structure of the ionophore. The same is true of the hydrophobic dye since absorbance changes have been demonstrated even in cases where the only interactions between the dye and ionophore are hydrophobic interactions. The dye can be either a separate molecule from the ionophore or can be attached to the ionophore by a covalent or polar bond or bonds. The micelle-forming material can be a separate chemical compound or it can be one of the other components; i.e., the ionophore or dye can itself be capable of forming micelles in aqueous environments.

The micelles utilized in the present invention are generally prepared from surfactants. A surfactant is an amphiphilic molecule having both polar and nonpolar sections. Soaps and detergents are typical surfactants, the term soap generally being reserved for salts of fatty acids and the term detergent generally being reserved for alkyl benzene sulfonates, alkyl sulfonates, and the like, such as sodium dodecyl sulfate. Both ionic and non-ionic surfactants exist, ionic surfactants generally being present as non-polar (e.g., hydrocarbon-containing) organic molecules containing carboxylate or sulfate group(s) in localized regions of the molecule. Non-ionic surfactants generally consists of organic molecules containing a polar and a non-polar region. Examples of non-polar surfactants include alkyl glucosides having a $C_6$-$C_{20}$ alkyl group and alkyl polyoxyethylenes. Bile salts, such as sodium cholate and sodium deoxycholate, along with soaps, are examples of ionic surfactants. Mixtures of surfactants are also suitable and can in some cases provide additional solubility for dyes (such as trans-azobenzene, which is particularly soluble in 2.6:1 molar ratio of sodium n-octylbenzene-p-sulfonate and glycerol 1-mono-oleate). However, workable micelles can be formed either with homogeneous or mixed surfactants. Surfactants are well known, and their structure and synthesis need not be presented here in detail.

When a micelle-forming substance is added to an aqueous solution at extremely low concentrations, the individual molecules remain dispersed and micelles do not form. As the concentration of micelle-forming material increases, the individual molecules begin to associate and micelles form. The concentration at which micelles begin to form is known as the critical micellular concentration (CMC). At higher concentrations, additional micelles form, and there is an exchange of material in the micelles with micelle-forming material unassociated in solution.

Most micelles are spherical bodies with lipophilic interiors and hydrophilic exteriors facing the aqueous environment. A typical micelle of this structure can contain from about 10 to over 100 molecules. Some large and relatively flat molecules such as bile salts tend to associate as dimers but have historically been referred to as micelle-forming even though they do not exhibit the more typical spherical form discussed above. These flat dimer micelles nonetheless have a hydrophobic "interior" between the two molecules and have been shown to be effective in the practice of the present invention.

The micelle-forming material as utilized in the present invention will usually be present in an amount sufficient to reach the CMC in the final mixture. Concentrations greatly in excess of the CMC adversely affect the invention but there is usually a wide range of micelle-forming material concentration over which the invention performs well.

As indicated previously, the structure of the surfactant is not essential to the practice of the present invention as long as the surfactant is capable of forming a mixed micelle in an aqueous environment in the presence of the hydrophobic or amphiphilic dye and hydrophobic ionophore. Whether a given surfactant is suitable for practice with the present invention can readily be determined by simple experimentation, for example by attempting to form micelles by the techniques described in this specification. All of the following surfactant types can be utilized in the present invention: (a) soaps of fatty acids, rosin acids, and tall oil; (b) alkylarenesulfonates; (c) alkylsulfates, including surfactants with both branched-chain and straight-chained hydrophobes, as well as primary and second sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethyleneglycol, particularly the tall oil ester; (f) polyethyleneglycol ethers of alkylphenols; (g) polyethyleneglycol ethers of long-chain alcohols and mercaptans; (h) fatty acyldiethanolamides; and (i) block copolymers of ethyleneoxide and propyleneoxide. Examples of specific compounds include sodium cholate, sodium deoxycholate, sodium dodecylsulfate (SDS), and Triton X-100 (Octoxymol-(9-10)).

Micelles of the invention are generally prepared by mixing a surfactant, a hydrophobic or amphiphilic dye, and a hydrophobic ionophore. Micelles are formed in the presence of an aqueous environment, so that water will also be present around the micelles. Sometimes water will be present in the interior of a hydrophobic layer of molecules, in which case the aggregation is generally referred to as a liposome. However, for ease of discussion and to avoid unnecessarily repeating multiple terms, the term micelle as used in this specification refers both to classical micelles and to the materials referred to as liposomes, whether present as unilamellar or polylamellar liposomes. A number of reviews and individual articles have been published describing micelles. See, for example, Fisher et al., *Chemical Society Reviews* (1977) 6: 25–42 and the publications cited therein.

A mixture containing the micelle components and water is treated to form micelles by simple mixing or by any other techniques for forming micelles or liposomes, such as sonication or subjection to high sheer forces (such as by rapid stirring), which are typically used to form liposomes. The lipophilic components can be initially dissolved in a small amount of a water-miscible organic solvent, such as acetone or ethanol, to promote mixing. Micelles in the size range of from about $10^{-3}$ to 1 microns in diameter, preferably from $10^{-3}$ to $10^{-1}$ microns, are formed. The mixture from which the micelles are made can contain additional components, such as stabilizers. Stabilizers are particularly useful when the mixture is to be stored for an extended period of time after preparation. Typical stabilizers include salts (which also influence micelle size), alpha-tocopherol, butyrated hydroxy toluene (BHT) and other antioxidants such as ascorbic acid, and solvents such as acetone.

Although the relative amounts of the components can be varied to take advantage of particular properties of the components (for example, when a hydrophobic dye or ionophore contributes to the stability or formation of the micelle as well as performing its primary function), it is preferred to begin with dye, ionophore, and surfactant compounds in the respective percentages of 0.005–1%, 0.01–1%, and 0.05–3% by weight of the final mixture. Preferred initial proportions are in the range 1:2–10:10–13 by weight for dye, ionophore, and surfactant, respectively. It should be noted that the initial proportions by weight set forth above are for the final mixture and do not refer to the concentration of components in the micelles. The micelles will generally contain a lower proportion of the surfactant component since some of this component will remain in solution.

The term ionophore as used in this specification intends molecules capable of selectively forming a complex with a metal ion. The word selectively here indicates that the ionophore favors formation of a complex with the target ion to the substantial exclusion of forming complexes with other ions. The ionophores should bind the target ion tightly and specifically in the presence of the micelle-forming detergents. Affinity for the target ion should be greater than $10^3$ (preferably greater than $10^4$) L mole$^{-1}$. The relative affinity of the ionophore for the target ion and other ions present in the sample should be 3 times (preferably 10 times, more preferably 30 times) the inverse ratio of their typical concentrations in the sample. This can be expressed mathematically by the formula $K_A/K_B \geq 3C_B/C_A$, in which K represents an association constant, C represents a concentration, A indicates the target analyte, and B represents another ion present in the sample. For example, if potassium ion is being detected in human blood where $C_K$ is about 4 mM and $C_{Na}$ is about 140 mM, a coefficient of associated of 1000 L mole$^{-1}$ would be acceptable if the coefficient of association for sodium ions were 10 L mole$^{-1}$ or less.

It is recognized that not all ionophores are selective for individual ions but may be selective for classes of ions. For example, certain ionophores will preferentially form complexes with divalent ions to the exclusion of monovalent or trivalent ions or with both sodium and potassium ions. The terms ion should therefore be understood to represent either an individual ion or a class of ions, such as alkali metal ions, alkaline earth ions, trivalent ions, transition metal ions, or some other grouping of ions. Ionophores that selectively form complexes with physiological ions useful in clinical testing are preferred, particularly ionophores that are selective for potassium, sodium, lithium, calcium, magnesium, or iron ions.

There are a number of general organic structures capable of forming complexes with ions. These include cyclic polypeptides, such as valinomycin, which selectively binds to potassium ions. There are two general classes of ion-specific cyclic compounds. Monocyclic compounds are referred to as coronands. Polycyclic ion-specific compounds are known as cryptands. In addition to cyclic compounds, a number of open-chain structures are also known. Open-chain structures capable of binding with metal ions are known as podands. Ionophores, regardless of their classification into these groups, are typically polydentate compounds. Polydentate refers to the presence in the molecule of multiple donor atoms, such as oxygen, sulfur, and nitrogen, that are capable of donating their electrons to form multiple ligand bonds with the metal ion.

Included within coronands are the well-known crown ethers, which contain a monocyclic chain containing oxygen as the donor atoms. Compounds that contain other electron rich atoms, such as sulfur and nitrogen, are not considered to be crown ethers but are members of the general class, coronands. Cryptands, the polycyclic analogues of coronands, are typically bicyclic and tricyclic compounds that partially surround the target ion. Although podands include molecules with only one donor group, such molecules are generally not selective for particular ions since selectivity for all classes of ionophores is generally related to the formation of a space or chamber of a size to fit a particular ion. However, podands that contain a sequence of donor atoms in a chain will wrap around different ions more or less tightly and therefore demonstrate different association constants so that selectivity can exist. Examples of selective podands include polydentate linear and branched amines and compounds containing both oxygen and nitrogen, such as ethylenediaminetetraacetic acid (EDTA) and diethylenetriaminepentaacetic acid (DEPTA). Moleules such as EDTA and DEPTA are themselves insufficiently hydrophobic to be utilized in the practice of the present invention. However, these and other highly polar chelating agents can be derivatized with non-polar groups, such as alkyl and/or aromatic groups, in order to increase their hydrophobicity.

Numerous cyclic ionophores containing appended phenyl groups that act to increase solubility in non-polar solvents are disclosed in U.S. Pat. No. 4,367,072 (mentioned above). See especially columns 3–17 of the patent and the examples that follow. Numerous non-cyclic poly(oxyethylene) derivatives having an appended alkyl group (e.g., as dodecyl ethers) are disclosed in Yamagida et al., *Bull. Chem. Soc. Japan* (1977) 50: 1386–1390.

The hydrophobic ionophore and hydrophobic dye can be part of the same molecule, if desired. Pacey et al., *Anal. Lett.* (1980) 13: 1985–1091; Pacey et al., U.S. Pat. No. 4,436,923; and Voegtle et al., U.S. Pat. No. 4,367,072, disclose a number of such compounds.

Some specific ionophores that can be used in the practice of the present invention are set forth below.

| Ionophore | Cation |
|---|---|
| Valinomycin | K$^+$ |
| 4,7,13,16,21-Pentaoxa-1,10-diaza-bicyclo[8,8,5]tricosane (Kryptofix 221)* | Na$^+$ |
| 4,7,13,16,24-Hexaoxa-1,10-diaza-bicyclo[8,8,8]hexacosane (Kryptofix 222)* | K$^+$ |
| 4,7,13,18-Tetraoxa-1,10-diaza-bicyclo[8,5,5]eicosane (Kryptofix 211)* | Li$^+$ |
| 12-Crown-4 | Li$^+$ |
| 15-Crown-5 | Na$^+$,K$^+$ |
| 18-Crown-6 | K$^+$ |
| 2,3-Naphtho-15-crown-6 | K$^+$ |
| Dibenzo-18-crown-6 | K$^+$ |
| Dicyclohexano-18-crown-6 | K$^+$ |
| Monensin | Na$^+$ |

*Kryptofix is a registered trademark of E. Merck, Darmstast, Germany.

It is important that the ionophore be sufficiently hydrophobic and lipophilic so as to become associated with the micelle. One manner of measuring hydrophobicity is to determine the partition coefficient between an organic solvent, such as dichloromethane and water. It is preferred that ionophores (and dyes as discussed later) exhibit partition coefficients between dischloromethane and water of at least 5, preferably at least 10.

Hydrophobicity is also an important characteristic of the dye used in the practice of the invention. The exact interation between the ionophore and dye is not known although it is believed to occur as a result of hydrophobic interactions. The changes in these hydrophobic interactions that occur as a result of formation of a complex between the ionophore and the target ion give rise to the ability to detect the presence of the ion.

The dyes of the invention are usually insoluble in water although some of the dyes can form micelles by themselves. Accordingly, the dyes can be either hydrophobic or amphiphilic compounds. Dyes having a partition coefficient in dichloromethane/water of at least 2, preferably at least 5, and most preferably 10 or greater are satisfactory.

Since many dyes are aromatic compounds, some common structural features are seen in a number of dyes of the invention. Many dyes have at least two aromatic rings and one phenolic hydroxyl group. When dissolved in aqueous solutions of appropriate detergents (at a concentration $\leq 5\%$), the hydroxy pK will be in the range of $13 \geq pK \geq 3$ (preferably in the range 5–12, more preferably in the range 8–11). Detergents will typically change the pK values of the dyes. For example, the pK of phenolphthalein is increased 1-2 units in 3% sodium cholate and the pK of 7-(N-decyl)-2-methyl-4-(3',5'-dichlorophen-4'-one)indonaphthol is decreased by 1-2 units.

The ionized form of the dye should have absorbance in the range 400-800 nm with a maximum molar extinction greater than $10^3$ (preferably greater than $10^4$) L moles$^{-1}$ cm$^{-1}$. On ionization the dye spectrum should change significantly, with a $\Delta\epsilon_M$ of at least $10^2$, preferably at least $10^3$ L moles$^{-1}$ cm$^{-1}$. The wavelength for maximum absorbance should change to give $\Delta\lambda_{max}$ greater than 10 nm, preferably greater than 50 nm.

Since the dye is either hydrophobic or amphiphilic, it is rendered more soluble in water by appropriate detergents and forms complexes (micelles) with detergents as described herein. Typically, the dye solubility in water is increased by at least 3-fold (preferably 10-fold) by addition of 10% of a detergent. The partition coefficient for the dye between water and dichloromethane is also increased significantly (greater than 3-fold, preferably greater than 10-fold) by addition of 10% detergent to the aqueous phase. The dye spectrum in aqueous solution is also changed by the detergent, typically being dependent on the nature and concentration of the detergent.

The interaction of dye and detergent can readily be measured using electrophoresis of samples of dye solutions and detergents on the Beckman Paragon SPEII system. Interacting dye and detergent will comigrate under the influence of an electric field. Thus, in deoxycholate (a negatively charged surfactant), 7-(N-decyl)-2-methyl-4-(3',5'-dichlorophen-4'-one)indonaphthol moves toward the anode, whereas in Triton X-100 (a neutral surfactant) this dye remains at the origin. In cetyltriethylammonium chloride (a positively charged surfactant), the dye moves to the cathode. It should be noted that the electrophoresis described here is performed in a buffer containing no detergent so that the only surfactant present comes from the sample being tested.

Particularly preferred dyes include phenolphthalein, bromocresol purpose, cresophthalein, chlorophenol red, tetrabromophenol blue, thymophthalein, 5-aminoeosin, eosin-5-maleamic acid, 5-(N-dodecanoyl)aminoeosin, 5-(N-hexadecanoyl)aminoeosin, acid blue #45, and 7-(n-decyl)-2-methyl-4-(3',5'-dichlorophen-4'-one)indonaphthol.

It will be recognized by those skilled in the art that the terms hydrophilic, hydrophobic, and amphiphilic are relative terms. Even the most hydrophobic compounds are soluble in water to some theoretical (if not practical) extent. As used in this application, a hydrophobic compound is preferably one with a partition coefficient between water/dichloromethane of 0-0.2. A hydrophilic compound will have a partition coefficient in dichloromethane/water (the reverse combination) of 0-0.2. Compounds with intermediate partition coefficients are considered amphiphilic in the broadest sense of this term. However, compounds which are asymmetrically amphiphilic are preferred over symmetrical amphiphilic compounds since asymmetrical amphiphilic compounds will more readily form traditional micelles.

The method of the present invention can be used to detect metal ions in any aqueous environment. Examples include whole blood, serum, plasma, urine, saliva, environmental water (for example, from oceans, wells, streams, and lakes), wastewaters (for example, from sewage treatment plants, industrial wastes, and mine tailings), and industrial process waters (for example, from fermentation suspensions, drilling muds, and aqueous chemical processes).

A sample suspected of containing the target metal ion is typically contacted with the micelles prepared as described above. Although the relative proportions of micelles and sample can be varied, as is understood by those skilled in the art of analytical chemistry, it is useful to initially form a mixture of the micelle composition and sample containing about 0.05-3% by weight of the micelle-forming component, about 0.005-1% by weight of the dye component, and about 0.01-1% by weight of the ionophore. A preferred composition contains 0.2-1% detergent, 0.01-0.1% dye, and 0.05-0.5% ionophore. Sensitivity can be increased by increasing the relative proportion of the micelle composition in relation to the sample, while higher levels of ion present in the sample can be determined by lowering this ratio or by diluting the sample by a predetermined amount.

Contact between the lipophilic micelle and the sample can be insured by thoroughly mixing the combined sample/micelle composition. Mixing during a contact time of from 5 sec. to 1 min. is generally sufficient. The temperature during preparation of the micelles should be fixed. A workable range is 10°-50° C., preferably 20-40° C., and most preferably around 30° C. Reaction of form micelles is quite rapid at approximately 30° C. (requiring only a few seconds) with longer times being required at lower temperatures.

If desired, the micelles can be made by adding the micelle components directly to a sample and forming the micelles in the presence of the sample. This procedure can be carried out by spreading the micelle components (detergent, dye, and ionophore) as a dry film on a suitable surface, typically in a reaction vessel in which the reaction is to be carried out. Sample (after dilution if necessary) is allowed to flow over the film and thus dissolve the components. The micelle components also can be dissolved in organic solvents and added to the sample or dried to form a powder which is added to the sample.

Changes in absorbance of light can be detected and can be measured either qualitatively, semiquantitatively, or quantitatively. Presence of a particular ion may be qualitatively determined by the appearance or change of color to the eye of the observer. Semi-quantitative measurements can be made by comparing the color of a sample to the color of a standard sample or samples or to a color chart. Quantitative measures can be made in a spectrophotometer or other device capable of accurately measuring absorbance of light. Since the micelles are colloidal in size, the mixture is essentially homogenous and no separation of phases is required.

To present invention also includes compositions useful for the detection of a metal ion. These compositions will contain a hydrophobic dye, a hydrophobic ionophore, and a surfactant capable of forming a micelle in an aqueous environment, as described above. The dye, ionophore, and surfactant are present in proportions capable of forming the micelle in an aqueous environment. These proportions may vary substantially, depending on the individual characteristics of the components, as is described above. It is preferred tha the dye, ionophore, and surfactant be present in the respective percentages of 0.005-1%, 0.01-1%, and 0.05-3% by weight of the final mixture with the preferred respective initial proportions being 1:2-10:10-30 by weight with respect to be each other. Characteristics of the individual components of the composition are discussed above.

The composition may contain other components, such as stabilizers, biocidal compounds, and buffering agents. Suitable buffering agents include phosphate, glycine, acetate, imidazole, and Tris buffers.

The compositions may be provided in either aqueous or dry form. Water or a sample would be added to the dry form of the reagent to form the micelles. Aqueous compositions could be present either as micelles or in a form ready for mixing, sonication, or use of other techniques for forming micelles without requiring measured addition of water. Buffers providing a pH in the range from about 5.5 to about 11 are preferred in either case. Aqueous compositions containing from about 0.2% to 10% micelle-forming materials are preferred.

Compositions of the invention can be formed into kits for use in assays for target ions. A kit will benerally comprise a number of containers of measured amounts of the composition as described above. Additional containers will be provided containing measured amounts of the target ion for use as standards. Additionally and more likely, an aqueous micelle suspension containing fixed aliquote of standard to be disbursed prior to assay can be utilized as standards. The composition may also be included as part of a device to which a sample is directly added, such as the capillary flow device described in U.S. patent application Ser. No. 880,793, filed July 1, 1986. A capillary flow device adapted to separate plasma from whole blood is described in an application filed on Oct. 29, 1986 (serial number not yet assigned), which is identified as attorney docket number 24140/BIOT-6. The composition could be present in any of the locations in the capillary flow device described in these applications, most typically in a plasma-containing portion of the flow path.

The invention now being generally described, the same will be better understood by reference to the following examples which are provided for purposes of illustration and are not to be considered limiting of the invention unless otherwise specified.

EXAMPLE 1

Homogeneous $K^+$ assay in aqueous solution

Reagent was made by mixing:
0.2 ml 2,3-naphtho-15-crown-5 (100 mg/ml in acetone)
0.04 ml 5-(N-dodecanoyl)aminoeosin (50 mg/ml in acetone)
1.2 ml sodium cholate (10% w/v in water)
2.6 ml of 0.1M sodium phosphate pH 7.0

Solutions of alkali metal chlorides were made up with the concentration indicated in the table below in 10 mM sodium phosphate buffer pH 7.6 containing 0.13M sodium chloride and 5.0 mM sodium azide.

A colormetric response was demonstrated by mixing 0.02 ml aliquots of the reagent with 0.02 ml of the alkali metal chloride solutions, then measuring A(0.1 cm, 600 nm) against a blank containing no potassium chloride.

| $(K^+)$, mM | $(Na^+)$ mM* | $(Li^+)$ mM | ΔA |
|---|---|---|---|
| 0 | 0 | 0 | (0) |
| 5 | 0 | 0 | 0.057 |
| 10 | 0 | 0 | 0.093 |
| 20 | 0 | 0 | 0.142 |
| 0 | 20 | 0 | 0.003 |
| 0 | 0 | 20 | 0.001 |

*NB All the alkali metal chloride solutions contained $Na^+$ (approximately 0.15 M) in the solvent. Concentration given is that added in excess.

The results show a direct relationship between $(K^+)$ and absorbance. The response was specific since $Na^+$ and $Li^+$ caused no significant absorbance change. When the crown ether was omitted from the reagent there was no absorbance change due to $K^+$.

EXAMPLE 2

Homogeneous $K^+$ Assay Using Phenolphthalein

Reagent was made by mixing:
0.10 ml phenolphthalein (10 mg/ml in acetone)
0.10 ml 2,3-naphtho-15-crown-5 (100 mg/ml in acetone)
0.60 ml sodium cholate (10% w/v)
1.20 ml water Solutions of alkali metal chlorides were made up in 0.10M glycine (adjusted to pH 10.0 with LiOH) containing 0.20M NaCl.

A colorimetric response was obtained by mixing 0.2 ml reagent and 0.2 ml alkali metal chloride and measuring A(0.1 cm, 550 nm) against a blank containing no KCl.

| $K^+$ mM | $Li^+$ (additional to that present in solvent) | ΔA |
|---|---|---|
| 0 | 0 | (0) |
| 5 | 0 | −0.024 |
| 20 | 0 | −0.167 |
| 0 | 20 | −0.009 |

EXAMPLE 3

Homogeneous $K^+$ assay using 7-(n-decyl)-2-methyl-4-(3',5'-dichlorophen-4'-one)indonaphthol Reagent was made by mixing:
0.50 ml dye (10 mg/ml in acetone)
0.50 ml 2,3-naphtho-15-crown-5 (20 mg/ml in acetone)
9.00 ml sodium deoxycholate (0.1%)

Samples were KCl solutions dissolved in 20 mM sodium phosphate (pH 7.6) containing 0.13M NaCl and 5 mM $NaN_3$.

Assays were run by mixing 0.50 ml reagent and 0.50 ml sample then measuring A(1 cm, 600 nm) versus a water blank.

| KCl (mM) | A |
|---|---|
| 0 | 0.283 |
| 2 | 0.771 |
| 4 | 0.959 |
| 6 | 1.113 |
| 8 | 1.218 |
| 10 | 1.320 |
| 20 | 1.748 |

EXAMPLE 4

$K^+$ assay using dicyclohexano-18-crown-6

Reagent was made by mixing:

0.25 ml dicyclohexano-18-crown-6 (100 mg/ml in acetone)
0.25 ml phenolphthalein (10 mg/ml in acetone)
1.00 ml sodium cholate (10% w/v)
3.50 ml water Samples containing KCl or LiCl (20 mM) were dissolved in 0.1M glycine (adjusted to pH 9.3 with NaOH) containing 0.2M NaCl.

Assays were run by mixing 0.20 ml reagent and 0.20 ml sample then measuring A(0.1 cm, 550 nm) A(0.1 cm, 450 nm).

| Sample | ΔA |
| --- | --- |
| No additive | 0.185 |
| KCl | 0.054 |
| LiCl | 0.167 |

EXAMPLE 5

K+ assay using Kryptofix-222(4,7,13,16,21,24-Hexaoxa-1-10-diazabicyclo[8,8,8]hexacosane)

Reagent was made by mixing:
0.25 ml Kryptofix (100 mg/ml in acetone)
0.15 ml Phenolphthalein (10 mg/ml in acetone)
0.50 ml Sodium cholate (10%)
4.00 ml Water Samples and assays as in Example 4.

| Sample | ΔA |
| --- | --- |
| No additive | 0.376 |
| KCl | 0.265 |
| LiCl | 0.367 |

EXAMPLE 6

Na+ assay using Kryptofix-221(4,7,13,16,21-Pentaoxa-1,10-diazabicyclo[8.8,5]-tricosane)

Reagent was made by mixing:
0.10 ml Kryptofix-221 (100 mg/ml in acetone)
0.10 ml Phenolphthalein (10 mg/ml in acetone)
1.80 ml Lithium Cholate (2.0% w/v)

Samples were alkali metal chlorides dissolved at the indicated concentrations in 0.10M glycine and adjusted to pH 9.3 with LiOH.

Assays were run by mixing 0.20 ml reagent and 0.20 ml sample then reading A(0.1 cm, 554 nm).

| Alkali Metal Chloride added | Conc. mM | A |
| --- | --- | --- |
| — | — | 0.327 |
| NaCl | 5 | 0.254 |
| NaCl | 20 | 0.173 |
| KCl | 20 | 0.218 |
| LiCl | 20 | 0.332 |

All publications cited in this application are indicative of the level of skill of those skilled in the art to which this invention pertains. Each publications is individually incorporated herein by reference to the same extent and in the same location as if each publication had been individually incorporated by reference at the location where cited.

Although the foregoing has been described in some detail by way of illustration and example for purposes of clarity and understanding, it will be obvious to those skilled in the art that certain changes and modifications may be practiced within the scope of the appended claims.

What is claimed is:

1. A method for detecting the presence of a metal ion in an aqueous environment, comprising:
   contacting a micelle-forming material, a hydrophobic or amphiphilic dye, and a hydrophilic ionophore capable of selectively binding said ion, wherein said hydrophobic ionophore is a molecule separate from said dye, with a sample of said aqueous environment to form a micelle-containing mixture, and
   detecting a change in absorbance of light by said dye in said mixture, wherein said change in absorbance is dependent on binding of said hydrophobic ionophore to said ion.

2. The method of claim 1, wherein said dye has two or more aromatic rings and a phenolic hydroxyl with a pK in the range of 3–13.

3. The method of claim 1, wherein said dye is phenolphthalein, bromocresol purple, cresophthalein, chlorophenol red, tetrabromophenol blue, thymophthalein, 5-aminoeosin, eosin-5-maleamic acid, 5-(N-dodecanoyl)aminoeosin, 5-(N-hexadecanoyl)-aminoeosin, 7-(n-decyl)-2-methyl-4-(3',5'-dichlorophen-4'-one)indonaphthol, or acid blue #45.

4. The method of claim 1, wherein said micelle-forming material is present as an aqueous micelle contining composition comprising an aqueous buffer prior to said contacting.

5. The method of claim 1, wherein said micelle-forming material comprises about 0.05–3% by weight of said mixture, said dye comprises about 0.005–1% by weight of said mixture, and said ionophore comprises about 0.01–1% by weight of said mixture.

6. The method of claim 1, wherein said micelle-forming material is an organic surfactant.

7. The method of claim 6, wherein said surfactant is sodium cholate, sodium deoxycholate, a bile salt, sodium dodecyl sulfate, or a mixture thereof.

8. The method of claim 1, wherein said ionophore is a crown ether.

9. The method of claim 8, wherein said ionophore is 2,3-naphtho-15-crown-5 or dicyclohexano-18-crown-6 and said ion is potassium.

* * * * *

UNITED STATES PATENT AND TRADEMARK OFFICE
CERTIFICATE OF CORRECTION

PATENT NO.   :   4,820,647
DATED        :   April 11, 1989
INVENTOR(S) :    Gibbons It is certified that error appears in the above-identified patent and that said Letters Patent is hereby corrected as shown below:

Title page:

In the Abstract, line 7, "Compositions method" should read --Compositions used in practicing the method--.

In column 2, line 5, "repoted" should read --reported--.

In column 4, line 4, "Octoxymol-(9-10)" should read --Oxtoxynol-(9-10)--.

In column 4, line 50, "1:2-10:10-13" should read --1:2-10:10-30--.

In column 7, line 42, "bromocresol" and "cresophthalein" should read --bromcresol-- and --cresolphathlaein--.

In column 8, line 54, "To" should read --The--.

In column 9, line 19, "benerally" should read --generally--.

In column 9, line 25, "aliquote" should read --aliquots--.

In column 12, line 44, "contining" should read --containing--.

Signed and Sealed this

Sixth Day of March, 1990

Attest:

JEFFREY M. SAMUELS

Attesting Officer

Acting Commissioner of Patents and Trademarks

UNITED STATES PATENT AND TRADEMARK OFFICE
CERTIFICATE OF CORRECTION

PATENT NO.   :   4,820,647
DATED        :   April 11, 1989
INVENTOR(S)  :   Gibbons It is certified that error appears in the above-identified patent and that said Letters Patent is hereby corrected as shown below:

In column 12, line 24, "hydrophilic" should read --hydrophobic--.

Signed and Sealed this

Sixteenth Day of July, 1991

Attest:

HARRY F. MANBECK, JR.

*Attesting Officer*      *Commissioner of Patents and Trademarks*